US 6,815,236 B2

United States Patent
Kim et al.

(10) Patent No.: US 6,815,236 B2
(45) Date of Patent: Nov. 9, 2004

(54) METHOD OF MEASURING A CONCENTRATION OF A MATERIAL AND METHOD OF MEASURING A CONCENTRATION OF A DOPANT OF A SEMICONDUCTOR DEVICE

(75) Inventors: Tae-Kyoung Kim, Yongin (KR); Sun-Yong Choi, Sungnam (KR); Chung-Sam Jun, Suwon (KR); Kwang-Soo Kim, Yongin (KR); Koung-Su Shin, Suwon (KR); Jeong-Hyun Choi, Yongin (KR); Dong-Chun Lee, Gyeonggi-do (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 10/694,882

(22) Filed: Oct. 29, 2003

(65) Prior Publication Data

US 2004/0092046 A1 May 13, 2004

(30) Foreign Application Priority Data

Nov. 6, 2002 (KR) ................................ 10-2002-0068339

(51) Int. Cl.$^7$ .............................................. H01L 21/66

(52) U.S. Cl. ........................................ 438/16; 702/155

(58) Field of Search ..................... 438/16, 17; 701/155

(56) References Cited

U.S. PATENT DOCUMENTS 6,153,444 A * 11/2000 Nakano et al. ............... 438/16
6,633,831 B2 * 10/2003 Nikoonahad et al. ........ 702/155

FOREIGN PATENT DOCUMENTS

JP       10-70168       3/1998
KR    1997-0010665     3/1997

* cited by examiner

Primary Examiner—John F. Niebling
Assistant Examiner—Andre' C. Stevenson
(74) Attorney, Agent, or Firm—Lee & Sterba, P.C.

(57) ABSTRACT

A method of measuring a concentration of a material includes irradiating an infrared light onto a substrate having a layer including a first material and dopants, wherein the infrared light is partially absorbed by and partially transmitted through the substrate including the layer. Intensities of the infrared light absorbed in the first material and the dopants are computed according to light wave numbers by utilizing a difference between intensities of the infrared light before and after transmitting the substrate and layer and by utilizing a difference between intensities of the infrared light absorbed in the substrate and layer and absorbed in only the substrate. Concentrations of the dopants are obtained by utilizing a ratio of light wave number regions corresponding to predetermined intensities of infrared light absorbed in the dopants relative to light wave number regions corresponding to the predetermined intensity of infrared light absorbed in the first material.

14 Claims, 7 Drawing Sheets

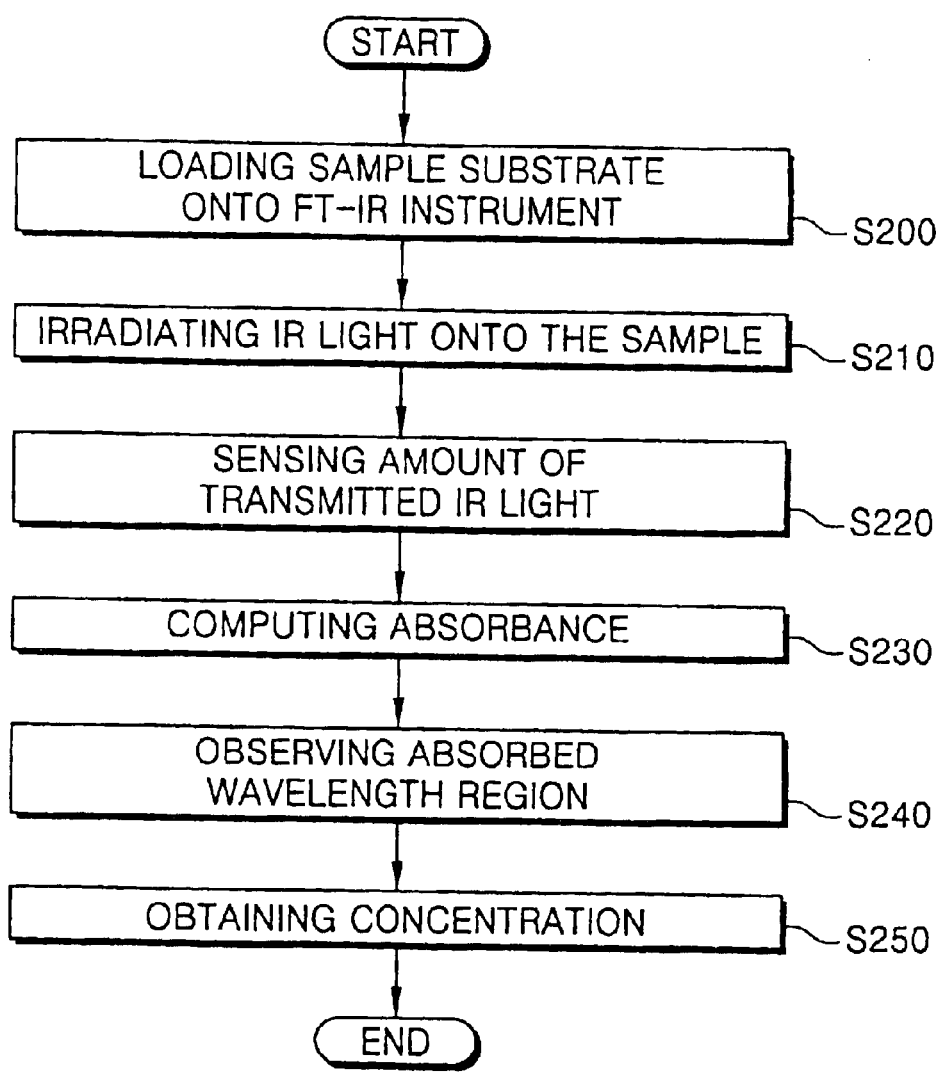

METHOD OF MEASURING A CONCENTRATION OF A MATERIAL AND METHOD OF MEASURING A CONCENTRATION OF A DOPANT OF A SEMICONDUCTOR DEVICE

BACKGROUND OF THE INVENTION

1. Field of the Invention

The present invention relates to a method of measuring a concentration of a material and a method of measuring a concentration of a dopant of a semiconductor device using the same. More particularly, the present invention relates to a method of measuring a concentration of a material contained in a boro-phosphorous silicate glass (BPSG) layer and a method of measuring a concentration of a dopant of a semiconductor device using the same.

2. Description of the Related Art

Recently, a degree of integration in semiconductor devices has increased to provide for faster processing of increased amounts of information and various techniques have been developed to facilitate information processing for a rapidly growing information society. In order to form increased numbers of patterns on a semiconductor substrate, a distance between patterns decreases and a width of a pattern narrows to form patterns having a relatively large step portion.

Generally, integrated patterns formed during manufacturing of a semiconductor device are transistors and various metal wirings formed on the semiconductor substrate. These integrated patterns are conductive, thus an insulation layer to insulate neighboring conductive layers should be formed between each pattern.

When the insulation layer is formed on the conductive pattern, which is formed on the semiconductor substrate, an upper surface of the insulation layer becomes uneven and crooked due to large stepped portions of the underlying patterns. Accordingly, when the conductive patterns and the insulation layers are repeatedly formed on the underlying patterns and layers, the unevenness of the layers formed later becomes significant, ultimately resulting in a formation of a device that does not function as a semiconductor device. Therefore, a method of forming an insulation layer filling gaps between patterns having large stepped portions and narrow intervals without forming internal voids and accomplishing planarization is an important technique.

An insulation layer is formed by depositing boro-phosphorous silicate glass (BPSG) because the gap-filling property or the planarizing property is improved by heating the deposited layer. A thus-formed BPSG layer has a good reflowing characteristic accompanying a property of changing viscosity rapidly through heating at a temperature of about 850° C. The planarizing degree of the BPSG layer is different depending upon the concentration of dopants contained in the BPSG layer at an identical temperature. Therefore, BPSG insulation layers having different dopant concentrations exhibit different insulating properties.

In order to lower a processing temperature during semiconductor processing, a concentration of dopants, such as boron (B), phosphorus (P) and the like, in silicon oxide ($SiO_2$), which is a primary component of the BPSG layer, is controlled to accomplish a good planarizing property at a low temperature. Accordingly, the measure of the intensity of the dopants, including boron and phosphorus, in the BPSG insulation layer is a very important inspection step.

A Fourier Transform Infrared Ray measurement (FT-IR measurement) may be used to analyze components contained in a layer.

A measuring instrument of an FT-IR analyzer is used for performing the FT-IR measurement. An absorption intensity distribution of IR for a target material is illustrated as a spectrum. When a radiant light passes through a layer of solid, liquid or gas, electrons, composing an atom, a molecule or an ion, absorb the radiant light to be transferred to an energy level corresponding to an absorbed photon energy of the radiant light. The difference between the electron energy levels is inherent to each chemical species. Therefore, the species composing the target material can be analyzed by inspecting a frequency of the absorbed radiant light. The frequency (c) is represented by an equation of $c=v/\lambda$. In this equation, $v$ represents a transferring velocity of a wave having a constant period and $\lambda$ represents a wavelength. An IR spectrum is illustrated by means of a wave number that is a reciprocal number of the wavelength.

In order to measure a concentration of each material included in a sample, a peak area at a peak region illustrated by each material in the IR spectrum is utilized. That is, the concentration of each material included in the sample may be noted by a relative size of the peak area illustrated by each material.

However, since a diameter of a measuring beam of the instrument is about 10 mm or larger, the beam is reflected and scattered by patterns formed on a substrate when the measurement is carried out on a BPSG layer formed on a semiconductor substrate. A distortion of the peak area due to the patterns is even more severe as a thickness of the BPSG layer increases.

In order to measure a concentration of a dopant in a BPSG layer during a semiconductor processing, a test sample is used. The test sample is obtained by forming a BPSG layer on a bare substrate using the same conditions as in the manufacturing process of the device. Then, the thickness and the concentration of the dopant are measured for the test sample and those of the BPSG layer are calculated using the measured result.

The test sample is formed considering various parameters to maintain the same state with a BPSG layer formed during actual semiconductor processing. However, when the sample is thick or when the intensity of the dopants in the sample is large, the intensity of the light transmitting the sample is insufficient so that detecting the transmitted light is difficult. In this case, the absorption intensity distribution is not illustrated clearly and a large numbers of split peaks are illustrated as noise around a main peak representing a specific material. Accordingly, the peak area cannot be calculated to precisely determine a concentration deviation. Thus, obtained data are unreliable.

In addition, a defect test and a concentration measurement for each processing step should be separately implemented, which increases overall processing time. Further, an additional process of forming the test sample must be implemented for every step of forming the BPSG layer during the semiconductor processing thereby increasing a manufacturing cost of the semiconductor device.

SUMMARY OF THE INVENTION

A first feature of the present invention is to provide a method of measuring concentration of a dopant using an infrared measurement, thereby obtaining reliable data even when an intensity of a transmitted light is small.

A second feature of the present invention is to provide a method of measuring concentration of a dopant using an infrared measurement, by which reliable data can be obtained even when an intensity of the transmitted light is very small thereby providing an unclear spectrum for some materials.

A third feature of the present invention is to provide a method of measuring concentration of a dopant of a semiconductor device, which can be repeatedly performed every time an insulation layer, including a dopant, is formed.

A fourth feature of the present invention is to provide a method of measuring concentration of a dopant of a semiconductor device, which can be applied along with actual semiconductor processing.

In accordance with a first aspect of the present invention, there is provided a method of measuring a concentration of a material including irradiating an infrared light onto a semiconductor substrate having a layer formed thereon, the layer including a first material and a plurality of dopants of which an entire intensity is less than an intensity of the first material, wherein a portion of the infrared light is absorbed in the semiconductor substrate including the layer and a remaining portion of the infrared light is transmitted through the semiconductor substrate including the layer; computing intensities of the infrared light absorbed in the first material and the plurality of dopants in accordance with light wave numbers by utilizing a difference between an entire intensity of the infrared light and an intensity of the infrared light transmitted through the semiconductor substrate including the layer and by utilizing a difference between an entire intensity of the infrared light absorbed in the semiconductor substrate including the layer and an intensity of the infrared light absorbed in only the semiconductor substrate; observing light wave number regions respectively corresponding to predetermined intensities of the infrared light absorbed in the first material and the plurality of dopants among all the light wave number regions absorbed in the first material and the plurality of dopants; and obtaining concentrations of each of the plurality of dopants by utilizing a ratio of the light wave number regions corresponding to the predetermined intensities of the infrared light absorbed in each of the dopants with respect to the light wave number region corresponding to the predetermined intensity of the infrared light absorbed in the first material.

In accordance with a second aspect of the present invention, there is provided a method of measuring a concentration of a material including irradiating an infrared light onto a semiconductor substrate having a layer formed thereon, the layer including a first material and a plurality of dopants of which an entire intensity is less than an intensity of the first material, wherein a portion of the infrared light is absorbed in the semiconductor substrate including the layer and a remaining portion of the infrared light is transmitted through the semiconductor substrate including the layer; computing intensities of the infrared light absorbed in the first material and the plurality of dopants in accordance with light wave numbers by utilizing a difference between an entire intensity of the infrared light and an intensity of the infrared light transmitted through the semiconductor substrate including the layer and by utilizing a difference between an entire intensity of the infrared light absorbed in the semiconductor substrate including the layer and an intensity of the infrared light absorbed in only the semiconductor substrate; observing light wave number regions respectively corresponding to predetermined intensities of the infrared light absorbed in the first material and the plurality of dopants among all the light wave number regions absorbed in the first material and the plurality of dopants; and obtaining concentrations of each of the plurality of dopants by utilizing a ratio of the intensity of the infrared light absorbed in each of the plurality of dopant corresponding to an entire light wave number regions with respect to the light wave number region corresponding to the predetermined intensity of the infrared light absorbed in the first material.

Preferably, the first material includes silicon and the plurality of dopants include boron and phosphorus. In addition, a plurality of conductive patterns may be formed on the semiconductor substrate.

The method may further include measuring an intensity of the infrared light absorbed in the semiconductor substrate, prior to forming the layer including the first material and the plurality of dopants on the semiconductor substrate.

In accordance with a third aspect of the present invention, there is provided a method of measuring concentrations of dopants in a semiconductor device including forming a plurality of conductive patterns on a semiconductor substrate; forming a first BPSG layer on the semiconductor substrate including the conductive patterns; irradiating a first infrared light onto the semiconductor substrate including the conductive patterns and the first BPSG layer, wherein a portion of the first infrared light is absorbed in the semiconductor substrate including the conductive patterns and the first BPSG layer and a remaining portion of the first infrared light is transmitted through the semiconductor substrate including the conductive patterns and the first BPSG layer; computing intensities of the first infrared light respectively absorbed in dopants included in the first BPSG layer in accordance with first light wave numbers by utilizing a difference between an entire intensity of the first infrared light and an intensity of the first infrared light transmitted through the semiconductor substrate including the conductive patterns and the first BPSG layer, and by utilizing a difference between an entire intensity of the first infrared light absorbed in the semiconductor substrate including the conductive patterns and the first BPSG layer and an intensity of the first infrared light absorbed in only the semiconductor substrate including the conductive patterns; and obtaining concentrations of a first boron dopant and a first phosphorus dopant by utilizing a ratio of the first light wave number regions corresponding to predetermined intensities of the first infrared light absorbed in the first boron dopant and the first phosphorus dopant of the first BPSG layer with respect to the first light wave number region corresponding to a predetermined intensity of the first infrared light absorbed in a first silicon of the first BPSG layer.

The method may further include forming a second BPSG layer on the first BPSG layer of which concentrations of the first boron and the first phosphorus are obtained; irradiating a second infrared light onto the semiconductor substrate including the second BPSG layer, wherein a portion of the second infrared light is absorbed in the semiconductor substrate including the second BPSG layer and a remaining portion of the second infrared light is transmitted through the semiconductor substrate including the second BPSG layer; computing intensities of the second infrared light respectively absorbed in a second silicon, a second boron dopant and a second phosphorous dopant included in the second BPSG layer in accordance with second light wave numbers by utilizing a difference between an entire intensity of the second infrared light and an intensity of the second infrared light transmitted through the semiconductor substrate including the second BPSG layer, and by utilizing a difference between an entire intensity of the second infrared light absorbed in the semiconductor substrate including the second BPSG layer and an intensity of the second infrared light absorbed in only the semiconductor substrate including the conductive patterns and the first BPSG layer; and obtaining concentrations of the second boron dopant and the second phosphorus dopant by utilizing a ratio of the second light wave number regions corresponding to predetermined intensities of the second infrared light absorbed in the second boron dopant and the second phosphorus dopant included in the second BPSG layer with respect to the second light wave number region corresponding to a predetermined intensity of the second infrared light absorbed in the second silicon of the second BPSG layer.

The measuring of the concentration of a dopant may be repeatedly performed more than twice.

In accordance with a fourth aspect of the present invention, there is provided a method of measuring concentrations of dopants in a semiconductor device including selecting a sample of a semiconductor substrate on which a BPSG layer is formed during a semiconductor device manufacturing process; obtaining an intensity of an infrared light absorbed in the BPSG layer formed on the sample with respect to a wave number of the infrared light; and obtaining concentrations of boron and phosphorus included in the BPSG layer formed on the sample by utilizing a ratio of light wave number regions corresponding to a predetermined intensities of the infrared light absorbed in the boron and the phosphorus with respect to a light wave number region corresponding to a predetermined intensity of the infrared light absorbed in a silicon included in the BPSG layer.

In the above method, when the concentrations of the boron and the phosphorus included in the BPSG layer as acceptable as required for the semiconductor device manufacturing process, the semiconductor device manufacturing process proceeds with the sample. In the alternative, the above method may further include removing the BPSG layer and forming a new BPSG layer including boron and phosphorus having newly adjusted concentrations on the semiconductor substrate when the concentrations of the boron and the phosphorus included in the previous BPSG layer is not acceptable as required for semiconductor device manufacturing process.

According to the present invention, additional manufacture of a test sample is not required to measure a concentration of a dopant, which decreases a processing cost. In addition, a thickness of a layer and the concentration of the dopant included therein can be measured simultaneously, which reduces a processing time.

BRIEF DESCRIPTION OF THE DRAWINGS

The above and other features and advantages of the present invention will become more apparent to those of ordinary skill in the art by describing in detail exemplary embodiments thereof with reference to the attached drawings in which:

FIG. 2 is a flow chart illustrating a method of measuring an IR spectrum of an insulation layer formed on a semiconductor substrate according to an embodiment of the present invention;

DETAILED DESCRIPTION OF THE INVENTION

Korean Patent Application 2002-68339, filed on Nov. 6, 2002, and entitled: "Method of Measuring a Concentration of a Material and Method of Measuring a Concentration of a Dopant in a Semiconductor Device," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
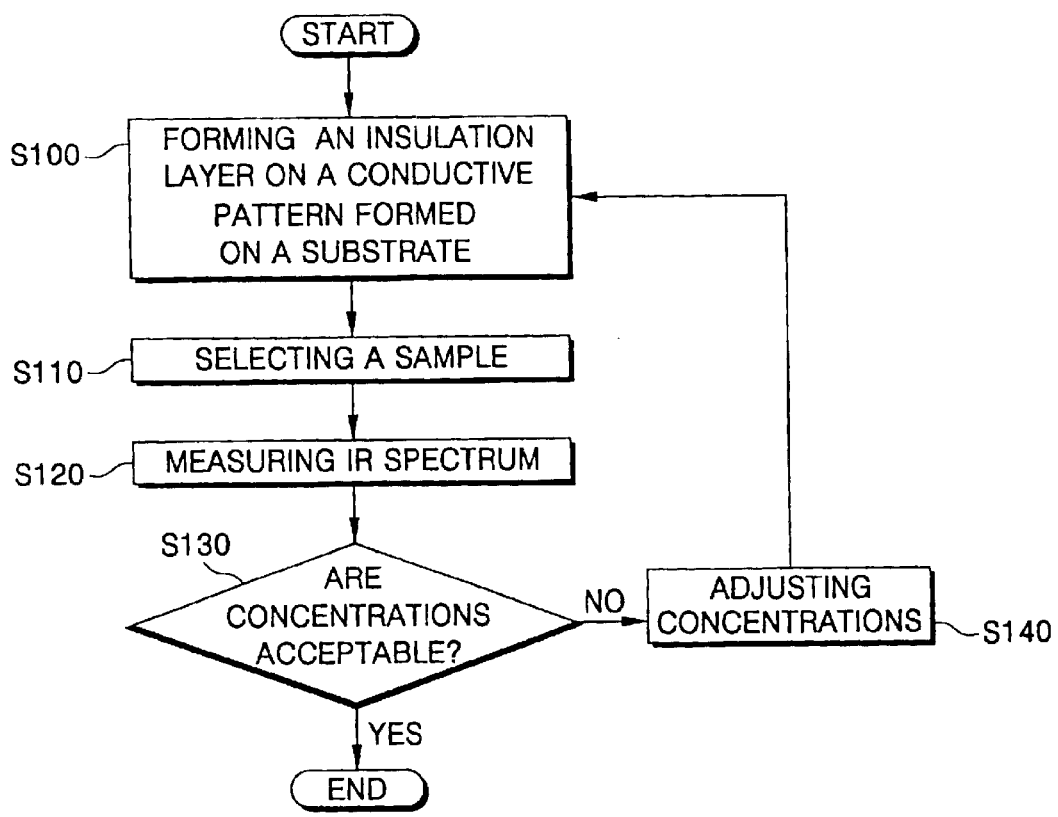
FIG. 1 is a flow chart illustrating a method of measuring a dopant concentration implemented during manufacturing a semiconductor device according to an embodiment of the present invention.

FIG. 1 is a flow chart illustrating a method of measuring a dopant concentration implemented during manufacturing a semiconductor device according to an embodiment of the present invention.

Referring to FIG. 1, a first conductive pattern is formed on a semiconductor substrate where an active region is defined. The first conductive pattern is an element of a semiconductor device, such as a transistor or various wirings. In order to insulate the first conductive pattern from the active region, in step S100, a first insulation layer is formed on the substrate on which the first conductive pattern is formed. The first insulation layer may be formed using borophosphorous silicate glass (BPSG) containing $SiO_2$, $B_2O_3$ and $P_2O_5$. Here, $SiO_2$ is included as a primary ingredient and $B_2O_3$ and $P_2O_5$ are included as dopants. In step S110, a substrate is selected as a sample after forming the first insulation layer thereon. In step S120, an IR spectrum of the first insulation layer formed on the substrate selected as the sample is measured.

FIG. 2 is a flow chart illustrating a method of measuring an IR spectrum of an insulation layer (step S120 of FIG. 1) formed on a semiconductor substrate according to an embodiment of the present invention.

Referring to FIG. 2, in step S200, the sample selected after the formation of the first insulation layer is loaded onto an FT-IR instrument. After a position of the substrate including the first insulation layer to be measured is selected, in step S210, IR light is irradiated onto the position of the substrate to be measured. Some portions of the IR light are partially absorbed in the first insulation layer while other portions of the IR light transmit the position of the substrate including the first insulation layer. The transmitted IR light is irradiated onto a sensor so that, in step S220, the sensor detects an intensity of the transmitted IR light. More specifically, an intensity of the absorbed IR light is determined by comparing an entire intensity of the IR light irradiated onto the first insulation layer with the intensity of the transmitted IR light passing the first insulation layer. The intensity of the IR light is represented as an absorbance with arbitrary units in accordance with selected conditions of the FT-IR instrument and is illustrated as a wave number of the irradiated IR light to give an absorption spectrum.

Figure 3A:
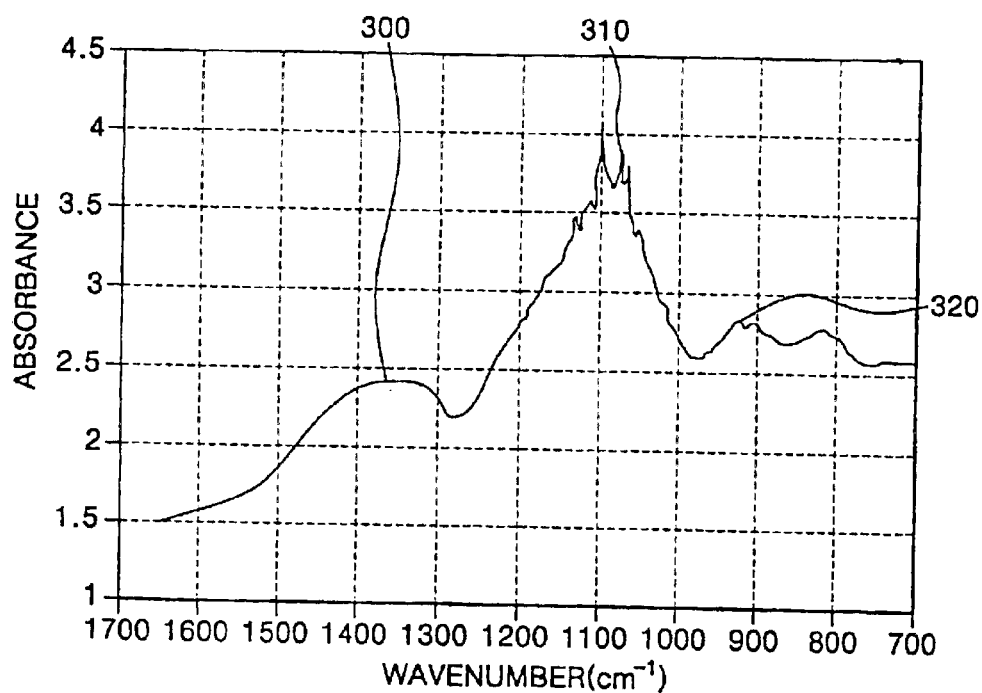
FIG. 3A is a graph illustrating a first IR spectrum obtained after forming a first insulation layer including BPSG on a semiconductor substrate according to an embodiment of the present invention.

FIG. 3A is a graph illustrating a first IR spectrum obtained after forming a first insulation layer including BPSG on a semiconductor substrate according to an embodiment of the present invention.

Referring to FIG. 3A, the first IR spectrum corresponding to a substrate having a first insulation layer including BPSG formed thereon illustrates an absorbance of materials included in the first insulation layer.

As for absorption wavelength regions of specific materials (including the dopants) such as phosphorus (P), silicon (Si) and boron (B), a first peak 300 corresponds to a material including phosphorus (hereinafter, referred to as "phosphorus"), a second peak 310 corresponds to a material including silicon (hereinafter, referred to as "silicon"), and a third peak 320 corresponds to a material including boron (hereinafter, referred to as "boron"). The first through third peaks 300, 310 and 320 indicate strong absorbance. However, the first IR spectrum also includes the absorbance of the substrate as well as the absorbance of the specific materials included in the first insulation layer.

Figure 3B:
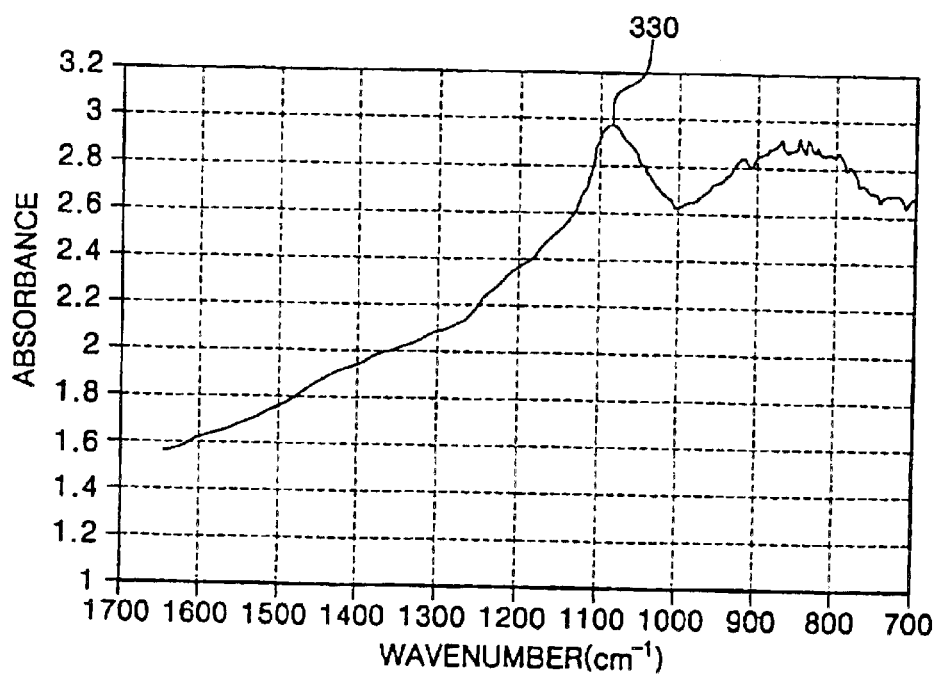
FIG. 3B is a graph illustrating a second IR spectrum obtained before forming a first insulation layer including BPSG on a semiconductor substrate according to an embodiment of the present invention.

FIG. 3B is a graph illustrating a second IR spectrum obtained before forming a first insulation layer including BPSG on a semiconductor substrate according to an embodiment of the present invention.

Referring to FIG. 3B, the fourth peak 330 corresponds to silicon at silicon absorption wavelength regions of the second IR spectrum because the semiconductor substrate having a first conductive pattern formed thereon was composed of silicon before the first insulation layer is formed on the semiconductor substrate.

Figure 3C:
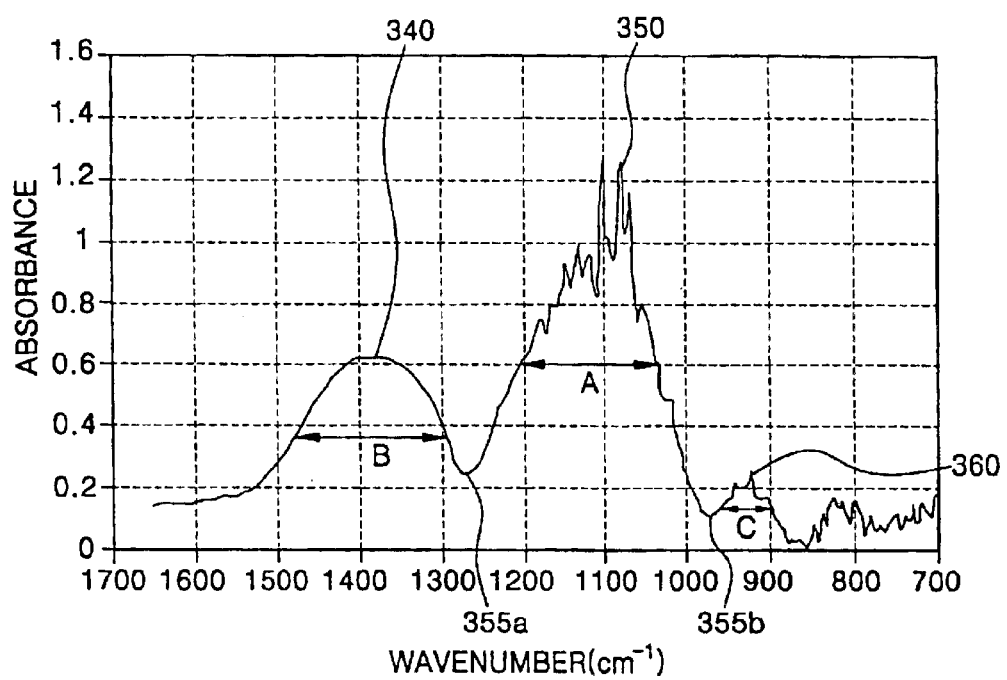
FIG. 3C is a graph illustrating a third IR spectrum of the first insulation layer obtained using a spectrum difference between the first and second IR spectrums shown in FIGS. 3A and 3B, respectively.

FIG. 3C is a graph illustrating a third IR spectrum of the first insulation layer obtained using a spectrum difference between the first and second IR spectrums shown in FIGS. 3A and 3B.

Referring to FIG. 3C, the third IR spectrum illustrating the absorbance of the pure first insulation layer was obtained from the spectrum difference between the first and the second IR spectrums in step S230 of FIG. 2. Here, the second IR spectrum of the semiconductor substrate where the first conductive pattern was formed was previously measured and stored in the FT-IR instrument. The first IR spectrum of the semiconductor substrate where the first insulation layer was formed was also previously measured and stored in the FT-IR instrument. Accordingly, in the third IR spectrum, a fifth peak 340 represents phosphorus, a sixth peak 350 represents silicon and a seventh peak 360 represents boron. The fifth through the seventh peaks 340, 350 and 360 illustrate strong absorption in the same absorption light wave number regions of the phosphorus, the silicon and the boron in the first IR spectrum. However, the third IR spectrum exhibits absorbance intensity different from that of the first IR spectrum.

When inspecting the first and third IR spectrums, the absorbance decreases from the center portions of the phosphorus absorption peak, silicon absorption peak and boron absorption peak. In some light wave number regions, the absorbance proportionally decreases according to an increasing distance from the wave number of each peak. As described above, the absorbance of one of the specific material decreases with an apex of the corresponding peak and a line representing the absorbance meets neighboring lines of other specific materials at the lowest points of the absorbance, namely, at the inflection points.

In the third IR spectrum, for example, the sixth peak 350 representing silicon included in the first insulation layer is located in a light wave number region between two inflection points 355a and 355b where the absorbance is relatively low. Here, the two inflection points 355a and 355b are adjacent to the light wave number regions of the phosphorous and the boron, respectively. In step S240 of FIG. 2, in the light wave number region where the sixth peak 350 is present, a first light wave number region difference (A) (that is, a width of the sixth peak 350 corresponding to one predetermined absorbance) is observed. Then, still in step S240, a second light wave number region difference (B) (that is, a width of the fifth peak 340 corresponding to the phosphorus adjacent to one inflection point 355a and representing another predetermined absorbance) is also observed. Further, in step S240, a third light wave number region difference (C) (that is, a width of the seventh peak 360 corresponding to the boron adjacent to another inflection point 355b and representing still another predetermined absorbance) is observed. Using the ratio of the second light wave number region difference (B) relative to the first light wave number region difference (A) and a ratio of the third light wave number region difference (C) relative to the first light wave number region difference (A), in step S250, the concentrations of the boron and the phosphorus contained in the BPSG layer can be obtained. According to the above-described method, the concentration of the specific material (e.g., a dopant) can be precisely obtained even though a peak may be divided into many branches, such as the sixth peak 350 in FIG. 3C.

When a peak is formed distinctively such as the fifth peak 340, however, the concentration of the specific material also can be obtained using a ratio relative to a peak area instead of the difference of the light wave number regions. That is, the concentration of the phosphorus may be obtained using a ratio between the area of the fifth peak 340 and the first light wave number region difference (A). Here, a conversion variable to obtain the correct concentration is different from a variable to compute the concentration using the difference of the light wave number regions.

The selected sample to obtain the concentrations of the specific materials may also be utilized for a defect detecting process. Accordingly, these two processes can be carried out using one selected sample.

Referring back to FIG. 1, as described above, each inflection point of all the specific materials included in the first insulation layer is observed to obtain the concentrations of each material. Then, in step S130, the concentrations of the specific materials are compared with references so that it may be determined whether the concentrations of the specific materials are acceptable. When the concentrations of the specific materials are acceptable, a subsequent process may then be performed. However, when the concentrations of the specific materials are not acceptable, the first insulation layer is removed and, in step S140, the concentrations of the materials are adjusted, and a new first insulation layer having the adjusted BPSG concentration is formed on the substrate.

In further processing, a contact may be formed through the first insulation layer, if required. In addition, an opening may be formed at a predetermined portion of the first insulation layer in consideration of a subsequent process, if necessary.

A second conductive pattern may then be formed on the first insulation layer formed on the substrate. The second conductive pattern may be a bit line, a capacitor or another wiring of a semiconductor device.

The same method for measuring a concentration of a specific material in the first insulation layer is employed to obtain a concentration of a specific material contained in the second insulation layer.

To insulate the second conductive pattern, a second insulation layer including BPSG is formed on the second conductive pattern and the first insulation layer. After one substrate where the second insulation layer is formed is selected as a sample, the sample is loaded onto an FT-IR instrument. The IR spectrums of the second insulation layer are measured in accordance with the above-described method.

However, when a second insulation layer is present, the irradiated IR light is partially absorbed by not only the second insulation layer but also the first insulation layer that includes dopants substantially identical to those of the second insulation layer when the IR light pass through the semiconductor substrate having the second and first insulation layers formed thereon. Accordingly, the intensities of the IR light absorbed by the first and second insulation layers are computed by the intensity of the transmitted IR light sensed using a sensor and an entire intensity of the IR light before the IR light does not transmit the semiconductor substrate. More specifically, the total absorption intensity of the IR light is obtained by summing the intensity of the IR light absorbed into the second insulation layer and the intensity of the IR light absorbed into the first insulation layer. In addition, since the substrate includes silicon, the total absorption intensity of the IR light also includes the intensity of the IR light absorbed into the substrate and the intensity of the IR light absorbed into the second conductive pattern or the intensity of the IR light reflected from the second conductive pattern. Therefore, the absorption spectrum of the second insulation layer is computed by a difference between spectrums obtained before and after the formation of the second insulation layer.

The absorption spectrum of the second insulation layer includes peaks having strong absorbance at inherent light wave number regions of the specific materials as illustrated in the absorption spectrum of the first insulation layer. The absorbance decreases according to a distance from the center portions of each peak and has an inflection point when the absorbance meets neighboring inherent wave number peaks represented by other materials included in the second insulation layer. From the inflection point, the absorbance increases again.

The concentrations of the specific materials included in the second insulation layer are obtained in the same manner employed for obtaining the concentrations of the specific materials included in the first insulation layer.

When the obtained concentrations of the specific materials are acceptable, a subsequent process may be executed. If the obtained concentrations of the specific materials are not acceptable, the second insulation layer is removed and a new second insulation layer having an adjusted BPSG concentration is formed. As described above, the concentrations of the dopants contained the insulation layer can be obtained using the IR spectrums of the insulation layer after forming the insulation layer on the substrate.

According to the method of the present invention, a presence of a defect can be observed after completing each step and also an acceptable insulation layer can be formed advantageously. Conventionally, a concentration test using a test sample and a defect test using a practical processing sample have been performed by two separate ways thereby slowing an overall processing time. However, since these two tests can be performed simultaneously using one processing sample according to the method of the present invention, a processing time can be greatly reduced.

Figure 4A:
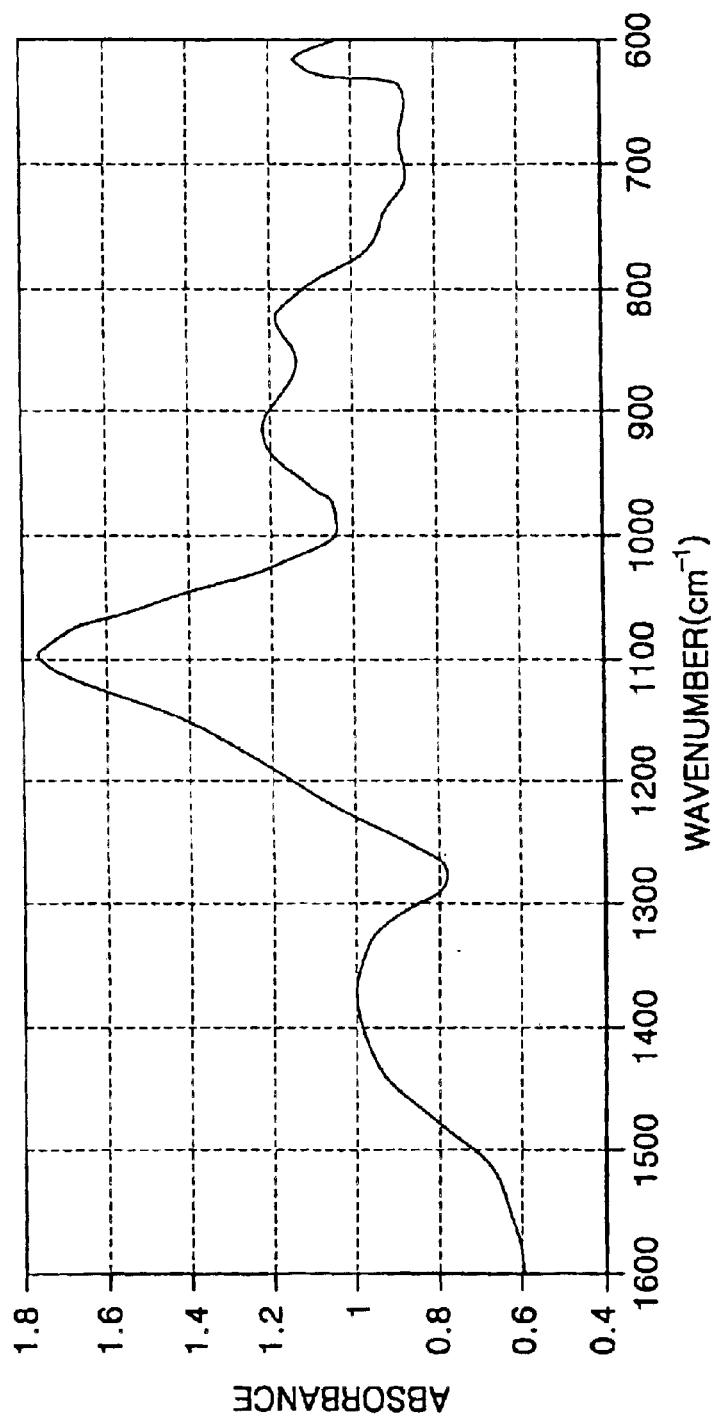
FIG. 4A is a graph illustrating a fourth IR spectrum of an insulation layer including BPSG formed on a substrate.

Comparative Verification of Reliability of Concentration Obtained Using Light Wave Number Region Difference FIG. 4A is a graph illustrating a fourth IR spectrum of an insulation layer including BPSG and formed on a substrate.

Referring to FIG. 4A, the IR spectrum of the BPSG layer formed on the substrate is represented by an absorbance of IR relative to a wave number. The fourth IR spectrum is obtained when the substrate is pervious to IR light and transmitted IR light through a thin film formed on the substrate are appropriately sensed. Since the peaks representing specific materials (dopants) such as silicon, boron and phosphorus are clear without divided branches in the fourth IR spectrum, the computing of the concentrations of the specific materials using a conventional method of measuring a concentration using spectrum distribution area may also be advantageously employed and the concentrations of the specific materials can be precisely obtained.

Figure 4B:
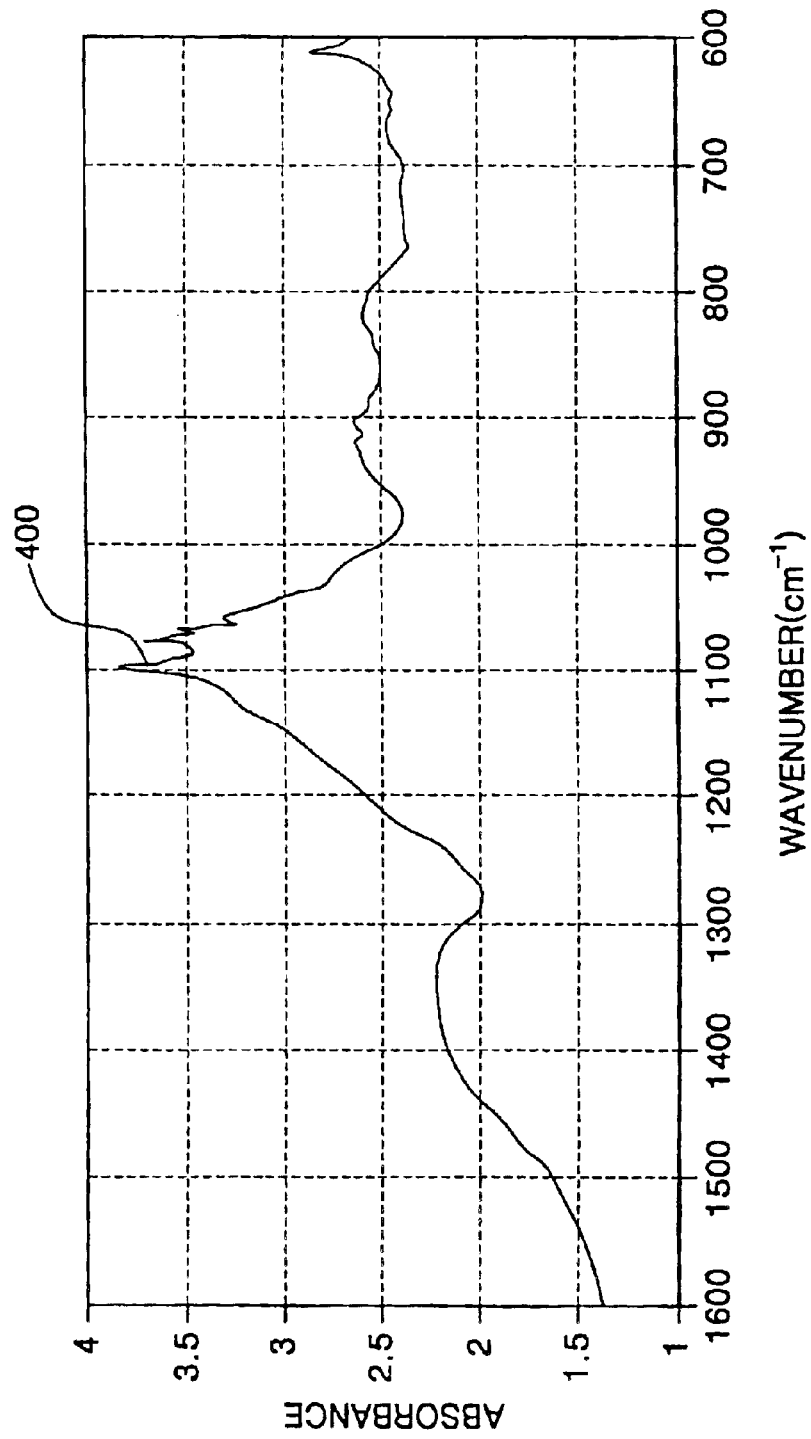
FIG. 4B is a graph illustrating a fifth IR spectrum of an insulation layer including BPSG formed on a substrate.

FIG. 4B is a graph illustrating a fifth IR spectrum of an insulation layer including BPSG and formed on a substrate.

Referring to FIG. 4B, an eighth peak 400 representing the strongest absorbance is not clear and is divided into many branches in the fifth IR spectrum. The eighth peak 400 is obtained when the substrate, on which a metallic layer is formed, is not pervious to light or when the intensity of transmitted IR light is small because a thick layer is formed on the substrate. In this case, the transmitted IR light is insufficient and could not be sensed well.

Accordingly, because the sensing of the transmitted IR light is obscure and computed absorbance obtained utilizing the intensity of the transmitted IR light is also obscure, the computing of the concentrations of the dopants may not be easily performed by the area. In addition, since the computing of the concentrations is not precise, the concentrations of the specific materials included in the layer are not precisely obtained.

However, when the concentration of the specific material is obtained using a width of the maximum peak in the IR spectrum, the concentration of the specific material can be computed irrespective of the shape of an apex of the maximum peak. Accordingly, correct concentration can be obtained even though several layers are formed on the substrate.

Figure 5A:
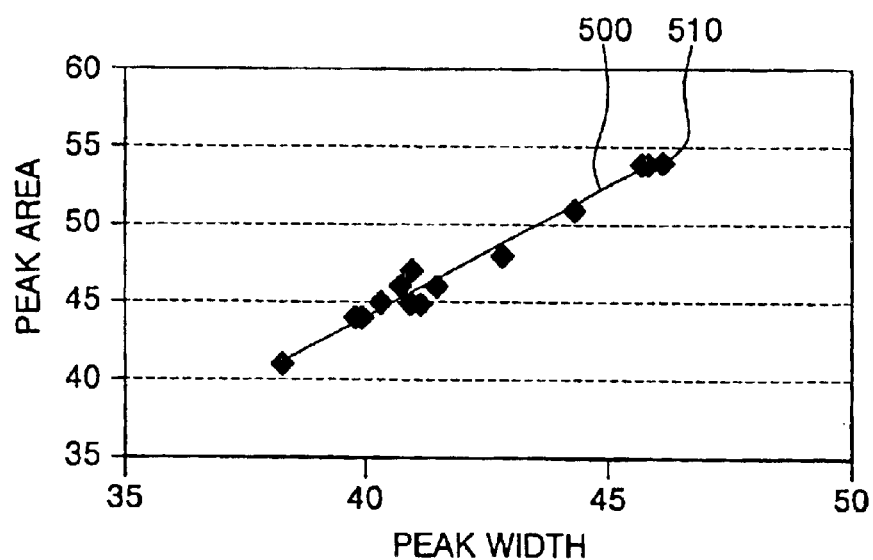
FIG. 5A is a graph illustrating a relationship between areas obtained by the method of the present invention and a conventional method utilizing spectrums having a distinct peak as illustrated in the fourth IR spectrum of FIG. 4A.

FIG. 5A is a graph illustrating a relation between areas perceived by the method of the present invention and the conventional method for spectrums having distinct peaks as illustrated in the fourth IR spectrum of FIG. 4A.

Referring to FIG. 5A, the concentration of the specific material is obtained based on the width of the peak, and an area of the peak reciprocally computed from the obtained concentration illustrates a constant relation with the width of the peak for one peak representing the same material in the IR spectrum of the BPSG layer when the shape of the spectrum is clear without divided branches. That is, the concentration of the material obtained by the conventional method and shown as a peak area denoted by a graph 500 and the concentration of the material obtained according to the method of the present invention and shown as a peak area denoted by a graph 510, are almost the same. Here, the unit of the peak width and the peak area are not designated for the sake of convenience.

Figure 5B:
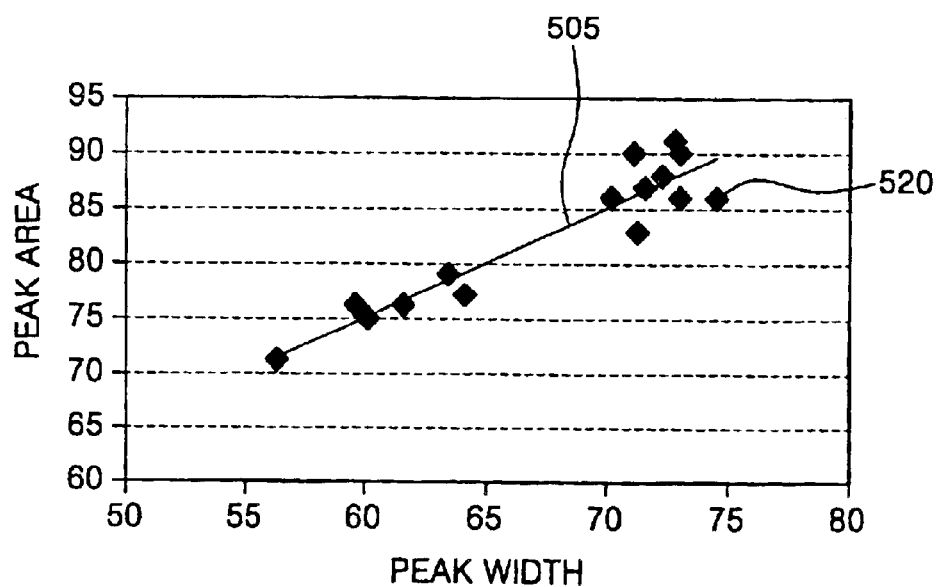
FIG. 5B is a graph illustrating a relationship between obtained by the method of the present invention and a conventional method utilizing spectrums having an indistinct peak as illustrated in the fifth IR spectrum of FIG. 4B.

FIG. 5B is a graph illustrating a relation between areas observed by the method of the present invention and the conventional method for spectrums having indistinct peaks as illustrated in the fifth IR spectrum of FIG. 4B.

Referring to FIG. 5B, because the peak is divided into many branches at the apex point in the IR spectrum and the intensity of the transmitted IR light is insufficient when the transmitted IR light are difficult to be sensed, the area obtained by the conventional method and denoted by a graph 520 and the area obtained by the size of the peak width according to the present invention and denoted by a graph 505 illustrate some deviation. This deviation represents a concentration deviation using the parameters of the peak width and the peak area. In the conventional method, the area was obtained considering the distribution of the peak at the apex point and the concentration was obtained using the obtained area. Thus, a large deviation was generated.

However, according to the present invention, the concentration of the specific material could be obtained irrespective of the effect of the sensing property of the IR light different from the conventional method, which is largely dependent on the sensing degree of the IR light. Since the method of measuring the concentration using the peak width according to the present invention is not affected by a division of the apex point, the obtained concentration of the specific material is very reliable.

As described above, an IR spectrum was measured for a selected sample when an insulation layer including BPSG was formed during a semiconductor device manufacturing process. To obtain a concentration of a specific material from a measured IR spectrum, a width of a specific light wave number region where a strong peak of absorbance according to the kind of the materials was utilized.

Since the concentration of the specific material is measured using the peak width of the IR spectrum, a precise concentration of the specific material can be obtained even though the substrate includes a thick insulation layer because the insulation layer including BPSG is formed several times, when the substrate including the layer is not pervious to light and has a low transmission to the IR light or when the concentration of the specific material in a target layer is high and a strong peak having a high absorbance is divided into several branches.

In addition, the concentration of the specific material can be measured at a defect test step simultaneously to reduce a manufacturing cost and processing time by omitting an additional process of forming a test sample for measuring the concentration of the specific material.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of measuring a concentration of a material comprising:

irradiating an infrared light onto a semiconductor substrate having a layer formed thereon, the layer including a first material and a plurality of dopants of which an entire intensity is less than an intensity of the first material, wherein a portion of the infrared light is absorbed in the semiconductor substrate including the layer and a remaining portion of the infrared light is transmitted through the semiconductor substrate including the layer;

computing intensities of the infrared light absorbed in the first material and the plurality of dopants in accordance with light wave numbers by utilizing a difference between an entire intensity of the infrared light and an intensity of the infrared light transmitted through the semiconductor substrate including the layer and by utilizing a difference between an entire intensity of the infrared light absorbed in the semiconductor substrate including the layer and an intensity of the infrared light absorbed in only the semiconductor substrate;

observing light wave number regions respectively corresponding to predetermined intensities of the infrared light absorbed in the first material and the plurality of dopants among all the light wave number regions absorbed in the first material and the plurality of dopants; and obtaining concentrations of each of the plurality of dopants by utilizing a ratio of the light wave number regions corresponding to the predetermined intensities of the infrared light absorbed in each of the dopants with respect to the light wave number region corresponding to the predetermined intensity of the infrared light absorbed in the first material.

2. The method of measuring a concentration of a material as claimed in claim 1, wherein the first material includes silicon and the plurality of dopants include boron and phosphorus.

3. The method of measuring a concentration of a material as claimed in claim 1, further comprising:

measuring an intensity of the infrared light absorbed in the semiconductor substrate, prior to forming the layer including the first material and the plurality of dopants on the semiconductor substrate.

4. The method of measuring a concentration of a material as claimed in claim 1, wherein a plurality of conductive patterns are formed on the semiconductor substrate.

5. A method of measuring a concentration of a material comprising:

irradiating an infrared light onto a semiconductor substrate having a layer formed thereon, the layer including a first material and a plurality of dopants of which an entire intensity is less than an intensity of the first material, wherein a portion of the infrared light is absorbed in the semiconductor substrate including the layer and a remaining portion of the infrared light is transmitted through the semiconductor substrate including the layer;

computing intensities of the infrared light absorbed in the first material and the plurality of dopants in accordance with light wave numbers by utilizing a difference between an entire intensity of the infrared light and an intensity of the infrared light transmitted through the semiconductor substrate including the layer and by utilizing a difference between an entire intensity of the infrared light absorbed in the semiconductor substrate including the layer and an intensity of the infrared light absorbed in only the semiconductor substrate;

observing light wave number regions respectively corresponding to predetermined intensities of the infrared light absorbed in the first material and the plurality of dopants among all the light wave number regions absorbed in the first material and the plurality of dopants; and obtaining concentrations of each of the plurality of dopants by utilizing a ratio of the intensity of the infrared light absorbed in each of the plurality of dopants corresponding to an entire light wave number regions with respect to the light wave number region corresponding to the predetermined intensity of the infrared light absorbed in the first material.

6. The method of measuring a concentration of a material as claimed in claim 5, wherein the first material includes silicon and the plurality of dopants include boron and phosphorus.

7. The method of measuring a concentration of a material as claimed in claim 5, further comprising:

measuring an intensity of the infrared light absorbed in the semiconductor substrate, prior to forming the layer including the first material and the plurality of dopants on the semiconductor substrate.

8. The method of measuring a concentration of a material as claimed in claim 5, wherein a plurality of conductive patterns are formed on the semiconductor substrate.

9. A method of measuring concentrations of dopants in a semiconductor device comprising:

forming a plurality of conductive patterns on a semiconductor substrate;

forming a first BPSG layer on the semiconductor substrate including the conductive patterns;

irradiating a first infrared light onto the semiconductor substrate including the conductive patterns and the first BPSG layer, wherein a portion of the first infrared light is absorbed in the semiconductor substrate including the conductive patterns and the first BPSG layer and a remaining portion of the first infrared light is transmitted through the semiconductor substrate including the conductive patterns and the first BPSG layer;

computing intensities of the first infrared light respectively absorbed in dopants included in the first BPSG layer in accordance with first light wave numbers by utilizing a difference between an entire intensity of the first infrared light and an intensity of the first infrared light transmitted through the semiconductor substrate including the conductive patterns and the first BPSG layer, and by utilizing a difference between an entire intensity of the first infrared light absorbed in the semiconductor substrate including the conductive patterns and the first BPSG layer and an intensity of the first infrared light absorbed in only the semiconductor substrate including the conductive patterns; and obtaining concentrations of a first boron dopant and a first phosphorus dopant by utilizing a ratio of the first light wave number regions corresponding to predetermined intensities of the first infrared light absorbed in the first boron dopant and the first phosphorus dopant of the first BPSG layer with respect to the first light wave number region corresponding to a predetermined intensity of the first infrared light absorbed in a first silicon of the first BPSG layer.

10. The method of measuring a concentration of a dopant as claimed in claim 9, further comprising:

forming a second BPSG layer on the first BPSG layer of which concentrations of the first boron and the first phosphorus are obtained;

irradiating a second infrared light onto the semiconductor substrate including the second BPSG layer, wherein a portion of the second infrared light is absorbed in the semiconductor substrate including the second BPSG layer and a remaining portion of the second infrared light is transmitted through the semiconductor substrate including the second BPSG layer;

computing intensities of the second infrared light respectively absorbed in a second silicon, a second boron dopant and a second phosphorous dopant included in the second BPSG layer in accordance with second light wave numbers by utilizing a difference between an entire intensity of the second infrared light and an intensity of the second infrared light transmitted through the semiconductor substrate including the second BPSG layer, and by utilizing a difference between an entire intensity of the second infrared light absorbed in the semiconductor substrate including the second BPSG layer and an intensity of the second infrared light absorbed in only the semiconductor substrate including the conductive patterns and the first BPSG layer; and obtaining concentrations of the second boron dopant and the second phosphorus dopant by utilizing a ratio of the second light wave number regions corresponding to predetermined intensities of the second infrared light absorbed in the second boron dopant and the second phosphorus dopant included in the second BPSG layer with respect to the second light wave number region corresponding to a predetermined intensity of the second infrared light absorbed in the second silicon of the second BPSG layer.

11. The method of measuring a concentration of a dopant as claimed in claim 10, wherein the measuring of the concentration of a dopant is repeatedly performed more than twice.

12. A method of measuring concentrations of dopants in a semiconductor device comprising:

selecting a sample of a semiconductor substrate on which a BPSG layer is formed during a semiconductor device manufacturing process;

obtaining an intensity of an infrared light absorbed in the BPSG layer formed on the sample with respect to a wave number of the infrared light; and obtaining concentrations of boron and phosphorus included in the BPSG layer formed on the sample by utilizing a ratio of light wave number regions corresponding to a predetermined intensities of the infrared light absorbed in the boron and the phosphorus with respect to a light wave number region corresponding to a predetermined intensity of the infrared light absorbed in a silicon included in the BPSG layer.

13. The method of measuring concentrations of dopants as claimed in claim 12, wherein the semiconductor device manufacturing process proceeds with the sample when the concentrations of the boron and the phosphorus included in the BPSG layer as acceptable as required for the semiconductor device manufacturing process.

14. The method of measuring concentrations of dopants as claimed in claim 12, further comprising:

removing the BPSG layer and forming a new BPSG layer including boron and phosphorus having newly adjusted concentrations on the semiconductor substrate when the concentrations of the boron and the phosphorus included in the previous BPSG layer is not acceptable as required for semiconductor device manufacturing process.

* * * * *